(12) United States Patent
Woods et al.

(10) Patent No.: US 6,231,714 B1
(45) Date of Patent: May 15, 2001

(54) ALLYLIC PHENYL ETHER (METH) ACRYLATE COMPOSITIONS AND NOVEL ALLYLIC PHENYL ETHER (METH) ACRYLATE MONOMERS

(75) Inventors: John G. Woods, Farmington; Susanne Morrill, West Hartford, both of CT (US); Ciaran B. McArdle, Dublin (IE)

(73) Assignee: Loctite Corporation, Hartford, CT (US)

( * ) Notice: Subject to any disclaimer, the term of this patent is extended or adjusted under 35 U.S.C. 154(b) by 0 days.

(21) Appl. No.: 09/198,536

(22) Filed: Nov. 24, 1998

(51) Int. Cl.[7] .................................................. B32B 31/00
(52) U.S. Cl. ...................... 156/275.7; 526/313; 526/320; 526/329.6
(58) Field of Search ................................ 526/329.6, 313, 526/320; 156/275.7

(56) References Cited

U.S. PATENT DOCUMENTS 2,459,835 * 1/1949 Monroe ................................ 526/313

(List continued on next page.)

FOREIGN PATENT DOCUMENTS 0 229 033    7/1987   (EP) .
0 234 450    9/1987   (EP) .

OTHER PUBLICATIONS

Chem. Abstract 78: 137333 r (1973).
Kato, et al. J. Polymer Science: Part A–1 6, 2493–3006 (1968).
Chem Abstract 67:11767 (1967).
Chem Abstact 90:152895 (1979).
Scranton et al., "Photopolymerization, Fundamentals and Applications", *American Chemical Society Symp. 673*, pp. 107–120, (1997).
Woods et al., "Alkenyloxystyrene Monomers for High–Temperture Adhesives and Sealants" *1997 American Chemical Society*, pp. 107–120, (1997).

Primary Examiner—John J. Gallagher
(74) Attorney, Agent, or Firm—Vidas, Arrett & Steinkraus

(57) ABSTRACT

Curable compositions include at least one monomer compound having both (meth)acrylic ester functionality and an allylic phenyl ether functional group on the same molecule, the allylic phenyl ether functional group having at least one unsubstituted position on the phenyl ring which is ortho or para to the allylic ether group, and a free radical catalyst system. The composition may also includes a latent thermally activated acid generator. Claisen Rearrangement of radically polymerized polymers produced from the compositions may be induced at temperatures of about 100° C. or more to give crosslinked products of improved thermal resistance. Novel monomers which may be used in such compositions are characterized by formulas I and II:

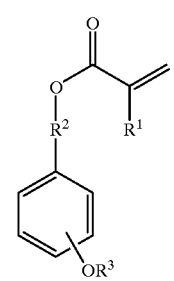

I

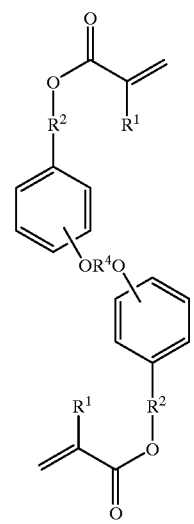

II where $R^1$ is H or methyl; $R^2$ is a direct bond, a group of the formula $-NC_nH_{2n}-$, or a group of the formula $-(OC_nH_{2n}-)_m-$ which when taken with the phenyl group to which it is attached forms a phenyl ether; n is 1–4 and m is 1–10; $R^3$ is $-CH_2CH=CH_2$, $-CH_2C(CH_3)=CH_2$, $-CH_2CH=CH(CH_3)$, $-CH_2C(CH_3)=CH(CH_3)$, $-CH_2CH=C(CH_3)_2$ or $-CH_2CH=CH(C_6H_5)$; and $R^4$ is a divalent allylic group, and wherein the compound is optionally substituted on a phenyl group thereof by an alkyl, alkoxy or halo group, provided that relative to the respective $-OR^3$ or $-OR^4O-$ groups, at least one unsubstituted ortho or para position remains on an adjacent phenyl ring.

29 Claims, 5 Drawing Sheets

U.S. PATENT DOCUMENTS

| | | |
|---|---|---|
| 2,647,882 | 8/1953 | Evans et al. . |
| 2,921,045 * | 1/1960 | Di Martino ............ 156/332 |
| 3,043,820 | 7/1962 | Krieble . |
| 3,457,212 | 7/1969 | Fukuoka et al. . |
| 3,855,040 | 12/1974 | Malofsky . |
| 3,923,737 | 12/1975 | George et al. . |
| 3,944,521 | 3/1976 | Bradley et al. . |
| 4,018,851 | 4/1977 | Baccei . |
| 4,044,044 | 8/1977 | Saito . |
| 4,259,117 | 3/1981 | Yamauchi et al. . |
| 4,295,909 | 10/1981 | Baccei . |
| 4,309,326 | 1/1982 | Sage et al. . |
| 4,380,613 | 4/1983 | Nativi . |
| 4,387,204 * | 6/1983 | Zahir et al. ............ 526/313 |
| 4,434,278 | 2/1984 | Skiscim . |
| 4,442,239 | 4/1984 | Tsunekawa et al. . |
| 4,447,588 | 5/1984 | Rametta . |
| 4,468,524 | 8/1984 | Zahir et al. . |
| 4,513,127 | 4/1985 | Jacobine . |
| 4,543,397 | 9/1985 | Woods et al. . |
| 4,622,348 | 11/1986 | Jacobine et al. . |
| 4,732,956 | 3/1988 | Woods et al. . |
| 4,764,239 | 8/1988 | Jacobine et al. . |
| 5,070,117 | 12/1991 | Klemarczyk et al. . |
| 5,084,490 | 1/1992 | McArdle et al. . |
| 5,141,970 | 8/1992 | McArdle et al. . |
| 5,211,877 | 5/1993 | Andrejewski et al. . |
| 5,369,200 | 11/1994 | Schadeli et al. . |
| 5,633,411 | 5/1997 | Woods et al. . |
| 5,641,850 | 6/1997 | Stohrer et al. . |

* cited by examiner

ALLYLIC PHENYL ETHER (METH) ACRYLATE COMPOSITIONS AND NOVEL ALLYLIC PHENYL ETHER (METH) ACRYLATE MONOMERS

BACKGROUND OF THE INVENTION

It is known from U.S. Pat. No. 5,084,490 and U.S. Pat. No. 5,141,970 that cationically cured propenyloxystyrene monomers have outstanding thermal and mechanical properties. The monomers undergo a 2-stage curing process involving an initial acid catalyzed addition polymerization or copolymerization of the styrene group (A-stage), followed by a heat-triggered post-curing reaction of the propenyloxyphenyl group (B-stage). During the post curing reaction, the A-stage polymer rearranges to form a reactive phenolic polymer, which spontaneously reacts with the propenyloxy group via an electrophilic substitution reaction. This results in the formation of a highly crosslinked polymer that exhibits a high decomposition temperature ($T_d$>400° C., TGA), a high glass transition ($T_g$>300° C., DMA) and good adhesion.

U.S. Pat. No. 5,369,200, Schädeli et al. (1994), describes terpolymers of two different maleimide monomers and an olefinically unsaturated phenyl ether monomer in which the phenyl ether is defined by an acid cleavable group —$OR_2$ linked to a phenyl ring. Examples of such monomers in this reference include a terpolymer of 4-(2-tetrahydropyranyloxy)benzyl methacrylate, N-hydroxymethylmaleimide and N-(acetoxymethyl) maleimide. The terpolymers are used as positive resists with acid generating photocatalysts and therefore it is imperative that the —$OR_2$ group be selected to be acid cleavable.

U.S. Pat. No. 5,211,877, Andrejewski et al, (1993) and U.S. Pat. No. 5,641,850 (Stoher et al) describe liquid-crystalline polyorganosiloxanes containing (meth)acryloxy groups. Also described are the monomers 4-(prop-2-ene-1-oxy)benzoic acid 4-methacryloxyphenyl ester and 4-(prop-2-ene-1-oxy)benzoic acid 4-(4-methacryloxybiphenyl)ester, U.S. Pat. No. 4,468,524, Zahir and U.S. Pat. No. 4,387,204, Zahir describe alkenylphenyl substituted acrylates or methacrylates and crosslinkable monomer compositions employing same.

Anaerobically curable compositions are a well known class of curable (meth)acrylate monomers composition. The compositions typically include polyfunctional monomers such as polyethylene glycol dimethacrylate (PEGMA), although some systems based on mono(meth)acrylates are known. The compositions also include a free radical catalyst system which is stabilized by atmospheric oxygen. The catalyst system usually include a hydroperoxide catalyst, typically cumene hydroperoxide, and at least one accelerator. Benzenesulfimide (saccharin) is a typical accelerator. Other common accelerators include acetyl phenyl hydrazine and dimethyl-para-toluidene. Deprivation of oxygen characteristically initiates cure (although initiation frequently also requires an additional condition to be simultaneously met, such as the provision of a source of metal ions or of heat). Anaerobically curable compositions are widely used as thread lockers, pipe joint sealants, gasketing agents, adhesives and as impregnation resins. To achieve a storage stability which is balanced based on access to atmospheric oxygen, other stabilizers are conventionally included in the composition.

It would be desirable to have anaerobically curable compositions which have improved high temperature resistance, especially a heat resistance capability comparable to the heat resistance of the B-staged cationically cured propenyloxystyrene monomer compositions described in U.S. Pat. No. 5,084,490 and U.S. Pat. No. 5,141,970.

SUMMARY OF THE INVENTION

The present invention pertains to curable formulations of monomers characterized as having both (meth)acrylic ester functionality and allylic phenyl ether functionality on the same molecule and the phenyl ring having at least one unblocked position ortho or para to the allylic ether group. Such compositions give high strength adhesive bonds when cured by a free radical mechanism. Further, the cured compositions are capable of thermally induced Claisen rearrangement, with or without an acid catalyst, thereby substantially improving the thermal stability of the cured polymer. A particularly surprising feature of the invention is that anaerobically curable compositions can be formulated using such monomers which give anaerobically cured adhesive bonds comparable to, or stronger than conventional anaerobic formulations based on multi-methacrylate monomers such as polyethylene glycol dimethacrylate (PEGMA).

One aspect of the invention therefore is a curable formulation comprising:

a) at least one monomer compound having both (meth) acrylic ester functionality and an allylic phenyl ether functional group on the same molecule, the allylic phenyl ether functional group having at least one unsubstituted position on the phenyl ring which is ortho or para to the allylic ether group, and b) a free radical catalyst system.

In certain embodiments the free radical catalyst is a free radical photoinitiator or an anaerobic curing catalyst system. The formulation may also include a latent thermally activated acid generator.

Another aspect of the invention comprises a method for bonding a pair of substrates, the method comprising:

i) applying a composition to a first of said substrates, the composition comprising:

a) at least one monomer compound having both (meth) acrylic ester functionality and allylic phenyl ether functionality on the same molecule, the allylic phenyl ether functional group having at least one unsubstituted position on the phenyl ring which is ortho or para to the allylic ether group, and b) an anaerobic curing catalyst system or a free radical photoinitiator system;

ii) joining a second substrate to the first substrate with the applied formulation therebetween so as to induce anaerobic curing of the applied formulation and form a bonded assembly; and subsequently iii) subjecting the bonded assembly to an elevated temperature of at least 100° C., preferably at least 150° C.

Yet another aspect of the invention comprises a method of preparing an anaerobically curable monomer comprising:

i) etherifying a phenolic hydroxyl group of a dihydroxybenzene or a phenol alcohol with an allylic etherifying agent, to give a hydroxy-substituted allylic phenyl ether compound; and then ii) esterifying said hydroxy-substituted allylic phenyl ether compound with an acrylic or methacrylic acylating agent.

Novel monomers useful in the formulations described above are a further aspect of the invention. Such compounds are characterized by formulas I and II:

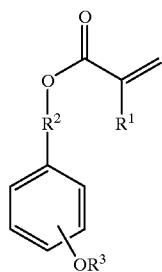

I

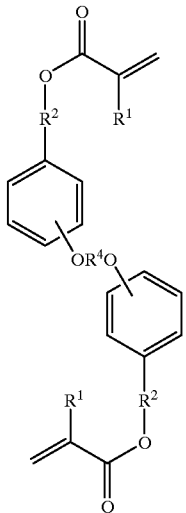

II where $R^1$ is H or methyl; $R^2$ is a direct bond, a group of the formula $-C_2H_{2n}-$, or a group of the formula $-(OC_nH_{2n}-)_m$ which when taken with the phenyl group to which it is attached forms a phenyl ether; n is 1–4; m is 1–10; $R^3$ is $-CH_2CH=CH_2$, $-CH_2C(CH_3)=CH_2$, $-CH_2CH=CH(CH_3)$, $-CH_2C(CH_3)=CH(CH_3)$, $-CH_2CH=C(CH_3)_2$ or $-CH_2 CH=CH(C_6H_5)$; and $R^4$ is a divalent allylic group, and wherein the compound is optionally substituted on a phenyl group thereof by an alky, alkoxy or halo group, provided that relative to the respective $-OR^3$ or $-OR^4O-$ groups, at least one unsubstituted ortho or para position remains on an adjacent phenyl ring. Polymers produced from such monomers, curable compositions employing such polymers, and methods for producing such polymers comprise further aspects of the invention.

DETAILED DESCRIPTION OF THE INVENTION

Figure 1:
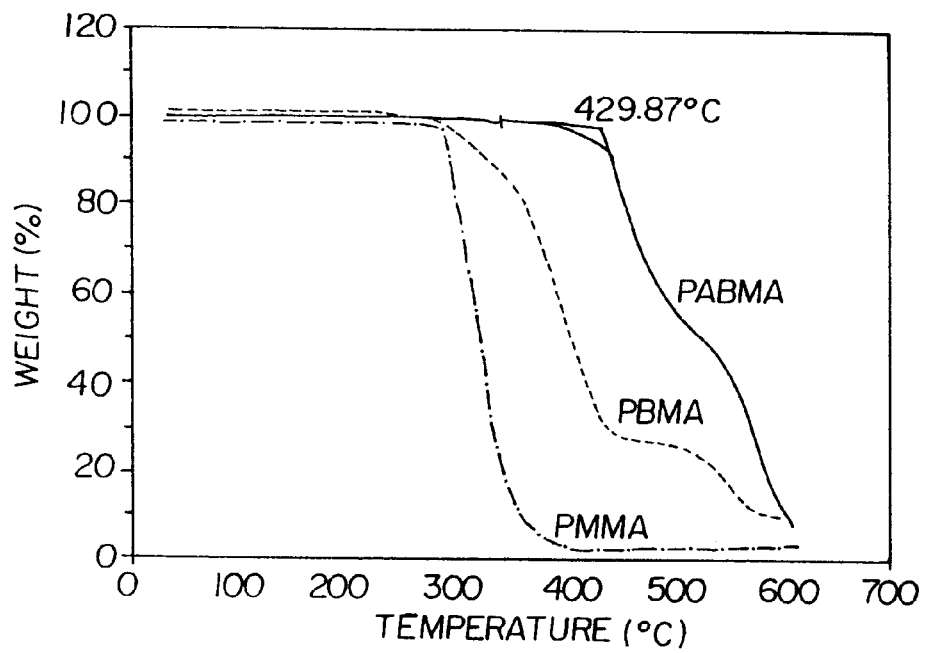
FIG. 1 is a TGA thermogram of a cured polymer of the invention (A+B stage cure) and of two comparative polymers, as described in Example 1.

For purposes of the present invention, the term "allylic group" refers to an organic functional group having at least three sequential aliphatic carbon atoms, defining respectively 1, 2 and 3 positions of the functional group, the 1-position carbon having two hydrogen atoms attached thereto and the group having a double bond between the 2 and 3 position carbon atoms. Specific examples of monovalent allylic groups include $-CH_2CH=CH_2$, $-CH_2C(CH_3)=CH_2$, $-CH_2CH=CH(CH_3)$, $-CH_2C(CH_3)=CH(CH_3)$, $-CH_2CH=C(CH_3)_2$ or $-CH_2CH=CH(C_6H_5)$. Specific examples of divalent allylic groups include $-CH_2CH=CHCH_2-$ and $CH_2=C(CH_2-)_2$. Where applicable, the allylic group may be the cis or trans configuration or a mixture of both.

The term "(meth)acrylate" refers to both acrylate and methacrylate. The term "(meth)acrylic refers to both acrylic and methacrylic.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

The compositions of the invention include at least one monomer compound having both (meth)acrylic ester functionality and allylic phenyl ether functional group on the same molecule, the allylic phenyl ether functional group having at least one unsubstituted position on the phenyl ring which is ortho or para to the allylic ether group. An unsubstituted ortho or para position, relative to the allylic ether groups, allows for the allylic group to be capable of Claisen Rearrangement. Polymers of such monomers when subjected to Claisen Rearrangement conditions give desirable high temperature resistance properties. If all of the ortho and para positions relative to the allylic phenyl ether group are blocked, polymer degradation via a cleavage reaction, rather than rearrangement, is the likely product of an acid catalyzed thermal reaction.

Specific examples of monomer compounds having a single (meth)acrylic ester functionality and allylic phenyl ether functional group on the same molecule and in which the allylic phenyl ether functional group is capable of Claisen Rearrangement include novel monomers of the invention characterized by formula I, above. Such compounds are suitably prepared by etherizing a 1,2-, 1,3- or 1,4- dihydroxybenzene or a 2-, 3- or 4-hydroxyphenyl alcohol with an allylic etherifying agent, to prepare a phenyl ether having a free phenolic or alcoholic hydroxy group and then esterifing that free hydroxy group with a suitable (meth)acrylic acylating agent. This procedure is preferable to one in which the ester is prepared first followed by etherification to improve yield of the esterification product, avoid ester hydrolysis during etherification or its workup, and because the intermediate ether may be more readily purified than a phenolic (meth)acrylate ester intermediate.

Suitably (the etherizing agent is a compound $R^3X$ where X is Cl, Br, or I and $R^3$ is as previously defined. Suitable acylating agents are acrylic and methacrylic acids, their anhydrides and their acid chlorides.) Acylation may also be accomplished by transesterification. The anhydrides and acid chlorides are preferred acylating agents.

Difunctional monomer compounds having both (meth) acrylic ester and allylic functionality and in which the allylic functionality is capable of Claisen Rearrangement, may be prepared in a similar manner except that the etherifying agent is an allylic dihalide and is reacted at a stochiometric ratio of about two moles of phenol to a single mole of the dihalide. Exemplary such dihalides are 1,4-dibromo-but-2- ene (Br—CH$_2$CH=CHCH$_2$—Br) and 2-chloromethyl-3-chloro-prop-1-ene (CH$_2$=C(CH$_2$ClS)$_2$). The resulting compounds are characterized by formula II, above. Mixtures of phenols can be used to give compounds in which the R$^2$ groups are substituted on their respective phenyl rings at different positions relative to the group —OR$^4$O—.

The dihydroxybenzene or a hydroxyphenyl alcohol starting compound may be optionally further substituted with one or more alkyl, alkoxy or halo groups, provided that after etherification, at least one ortho or para position on the phenyl ring, relative to the allylic ether group, will remain unsubstituted. Preferably the starting compound is one which will provide at least two unsubstituted positions ortho or para relative to the allylic ether group.

Specific novel compounds of the present invention include 4-allyloxyphenethyl methacrylate, 3-allyloxyphenethyl methacrylate, 2-allyloxyphenethyl methacrylate, 4-allyloxyphenyl methacrylate, 3-allyloxyphenyl methacrylate, 2-allyloxyphenyl methacrylate, 2-(allyloxyphenoxy)ethyl methacrylate, 3-(allyloxyphenoxy)ethyl methacrylate, 4-(allyloxyphenoxy)ethyl methacrylate, 2-allyloxybenzyl methacrylate, 3-allyloxybenzyl methacrylate, and 4-allyloxybenzyl methacrylate.

Other compounds which may be used in the invention as monomers having both (meth)acrylic ester and allylic phenyl ether functionality are reported in U.S. Pat. No. 5,641,850, namely:

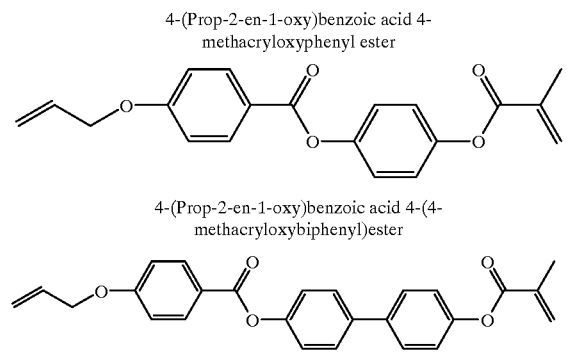

4-(Prop-2-en-1-oxy)benzoic acid 4-methacryloxyphenyl ester 4-(Prop-2-en-1-oxy)benzoic acid 4-(4-methacryloxybiphenyl)ester Curable formulations of the invention may be prepared based on one or more allylic phenyl ether (meth)acxylate monomers as the sole polymerizable component. However, in many instances it will be desirable to include as co-monomer a conventional radically polymerizable monomer. The co-monomer may range from 0 to 99% by weight of the total monomer employed in the composition. Suitable such conventional polymerizable co-monomers which may be included in the inventive formulations include the diacrylates and dimethacrylates described in U.S. Pat. No. 3,043,820 (Krieble), U.S. Pat. No. 3,457,212 (Fukuoka et al.), U.S. Pat. No. 3,923,737 (George et al.), and U.S. Pat. No. 3,944,521 (Bradley et al.). Other suitable polymerizable co-monomers include acrylate-terminated monomers such as the polyacrylate esters formed from organic polyisocyanates, such monomers being described, for example, in U.S. Pat. No. 3,425,988 (German et al.), U.S. Pat. No. 4,018,351 (Baccei), U.S. Pat. No. 4,295,909 (Baccei), U.S. Pat. No. 4,309,326 (Baccei), and U.S. Pat. No. 4,380,613 (Nativi).

Particularly suitable polyfunctional acrylates and methacrylates include triethylene glycol dimethacrylate, ethylene glycol dimethacrylate, tetraethylene glycol dimethacrylate, polyethylene glycol, diacrylate, polyethylene glycol dimethacrylate, 1,3-butylene glycol dimethacrylate, trimethylol propane trimethacrylate, neopentyl glycol dimethacrylate, ethoxylated bisphenol A dimethacrylate, propoxylated bisphenol C dimethacrylate and bisphenol A bis(2-hydroxypropyl)dimethacrylate.

Other monoacrylates and monomethylacrylates may also be employed in the compositions of the present invention as co-monomers. Suitable such other monoacrylates and monomethylacrylates include cyclohexyl methacrylate, 2-ethylhexyl methacrylate, hydroxyethyl methacrylate, isooctyl acrylate and n-butyl acrylate.

Methacrylic acid, acrylic acid, and similar α,β-unsaturated carboxylic acids may also be employed as co-monomers in the compositions of the present invention. Half-esters of α, β-unsaturated dicarboxylic acids, such as the 2-hydroxyethyl (meth)acrylate half-ester of maleic acid and those described in U.S. Pat. No. 3,428,614 (Brownstein) and U.S. Pat. No. 4,080,238 (Wolinski et al.), may likewise be used as co-monomers.

Poly(meth)acrylate functional reaction products of the aforementioned half-esters are also useful as co-monomers, such as those described in U.S. Pat. No. 4,209,604 (Weber).

Still other suitable co-monomers include the (meth)acrylate functional phosphorus containing monomers described in U.S. Pat. No. 4,044,044 (Saito), U.S. Pat. No. 4,259,117 (Yamauchi et al.), U.S. Pat. No. 4,434,278 (Skiscim) and U.S. Pat. No. 4,442,239 (Tsunekawa).

Acrylic and methacrylic functional silicones are yet another class of polymerizable monomers useful as co-monomers in the inventive compositions.

In order to enhance the shelf-life of the compositions of the present invention it may be desirable to remove metal ions, if such are present, from the polymerizable monomer. Removal of metal ions may be effected by means known to those skilled in the art.

The compositions of the invention further comprise an effective amount of a free radical initiator. If an anaerobically curing system is desired the initiator is desirably a member of the class consisting of hydroperoxides, of which cumene hydroperoxide and t-butyl hydroxide are examples; peroxyesters, such as t-butyl perbenzoate; peroxy carbamates (i.e., reaction products of hydroperoxides and isocyanates); and halogen containing compounds having electronic structures which facilitate free radical formation, as exemplified and described in U.S. Pat. No. 4,447,588. Typically an anaerobic initiator component will be present in an amount of 0.5–10 parts by weight per 100 parts of the monomer component.

Of the various classes of initiators described above, the peroxy initiators are generally preferred over the halogenated compounds with the hydroperoxides generally the most desirable.

It has been known since U.S. Pat. No. 3,046,262 and U.S. Pat. No. 3,218,305 to use saccharin (benzoic sulfimide) as an accelerator of anaerobically curing acrylic compositions. The same reference, and many since, teach that sulfimides generally are useful as accelerators. Sulfimides are compounds having a divalent group of the structure:

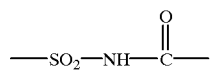

where both the sulfonyl and the carbonyl groups are linked to hydrocarbon groups. Other sulfimides or compounds which function analogously thereto are described in U.S. Pat. No. 4,513,127, U.S. Pat. No. 4,764,239 and U.S. Pat. No. 4,622,348. The anaerobically curable formulations of the present invention likewise will typically also include a sulfimide or sulfimide analog as an accelerator. Such compounds may be employed in an amount of 0.1 to 10% by weight of the composition, preferably 0.1 to 2.0%.

The inventive anaerobically curable compositions may also optionally include other co-accelerator ingredients in addition to sulfimide or sulfimide analog. Especially desirable are tertiary aromatic amines, particularly N,N-dimethyl-p-toluidine, N,N-diethyl-p-toluidine and N,N-dimethyl aniline. Other classes of useful co-accelerators are the hydrazine derivatives, such as 1-acetyl-2-phenylhydrazine, described in U.S. Pat. No. 4,287,330 and ferrocene or substituted ferrocene compounds as described in U.S. Pat. No. 3,855,040. Typical amounts of such co-accelerators are 0.01% to 10%, preferably 0.05% to 2% by weight.

The compositions of the invention may also include an inhibitor of polymerization in an amount effective to give desired shelf stability to the composition. Suitable inhibitors are well known to those skilled in the art and include those described in the aforementioned patents which described anaerobic compositions. Metal chelators, such as ethylenediaminetetraacetate (EDTA) and 1-hydroxyethylidine-1,1-diphosphonic acid (HEDPA), and quinone type inhibitors, such as hydroquinone, methyl hydroquinone, napthaquinone and benzoquinone, are preferred.

While the monomers described above are useful in anaerobic compositions, other curable compositions may also be formulated therewith. In particular UV and/or thermally curable formulations may also be readily formulated. UV curable formulations include a free radical photoinitiator such as acetophenone, chlorinated acetophenone, dialkoxyacetophenones, dialkylhydroxyacetophenones, dialkylhydroxyacetophenone esters, benzoin, benzoin acetate, benzoin alkyl ethers, dimethoxybenzoin, dibenzylketone, and other aromatic ketones, acyloxime esters, acylphosphine oxides, acylphosphonates, ketosulfides, dibenzoyldisulphides, and diphenyldithiocarbonate. Typically the free radical photoinitiator will be employed in an amount of 0.1 to 10%, preferably 0.5 to 5% and more preferably 1–2% by weight of the curable composition. Photoinitiators active in the visible wavelength range may be used to produce compositions curable with visible light.

Thermal initiators which may be employed include the various initiators described above for anaerobically curing compositions as well as diacyl peroxides such as benzoyl peroxide, azonitrile compounds such as 2,2'-azobis (isobutyronitrile) (AIBN), and substituted or unsubstituted benzopinacol. Effective amounts for thermal initiation are typically as follows: for peroxy compounds, 0.1–5% by weight of the compositions; for azonitrile compounds, 0.1–1% by weight of the compositions; and for benzopinacols, 0.1–2% by weight of the compositions.

In order to induce a B-stage cure by Claisen Rearrangement of the allylic phenyl ether group the radically cured polymer is subjected to an elevated temperature. Such a temperature is suitably at least 100° C., more preferably at least 150° C. A reaction time in the range of about 2–4 hours will generally be suitable at a temperature of about 150° C. At higher temperatures shorter times may be employed, while at lower temperatures longer times may be required. Typically Claisen Rearrangement reactions also require an acid catalyst to be present, and such catalysts can be beneficially employed in the invention. Surprisingly, however, at least some of the radically cured formulations of the invention have been observed to undergo Claisen Rearrangement even in the absence of an added acid catalyst. Therefore the provision of an acid catalyst for Claisen Rearrangement is considered optional.

Unlike systems based on styrene ether monomers, such as disclosed in U.S. Pat. No. 5,084,490; and U.S. Pat. No. 4,141,970, the (meth)acrylic monomers of the invention are not cationically curable and so an acid catalyst can be incorporated into the system without immediately inducing polymerization. However, for long term storage stability and activity of the monomer formulation it is suggested that if an acid catalyst is used it be a latent acid catalyst. In the case of a formulation containing a free radical photoinitiator, a cationic photoinitiator may also be used. Cationic photoinitiators, although they usually do produce both acid and radical species on exposure to UV, are generally not very effective in inducing polymerization of (meth)acrylate monomers. However they could be used effectively to provide acidic species in the composition cured with a traditional free radical photoinitiator. Suitable cationic photoinitiators include triarylsulfonium and diaryliodonium salts containing non-nucleophilic counterions and aryl diazonium salts. Specific examples include 4-methoxybenzenediazonium hexafluorophosphate, benzenediazonium tetrafluoroborate, diphenyl iodonium chloride, diphenyl iodonium hexafluorophosphate, 4,4'-dioctyloxydiphenyl iodonium hexafluorophosphate, triphenylsulfonium tetrafluoroborate, diphenyltolylsulfonium hexafluorophosphate, phenylditolylsulfonium hexafluoroarsenate, and diphenyl-thiophenoxyphenylsulfonium hexafluoroantimonate. A commercially available such material is Cyracure UVI 6974 sold by Union Carbide Corporation.

A thermal mechanism can also be used to generate an acid catalyst for Claisen Rearrangement. In the case of anaerobically cured adhesive compositions, this option allows for the acidic species to be generated long after the anaerobic cure and only at the time the Claisen Rearrangement is induced. Many of the compounds known as cationic photoinitiators are also effective as thermally activated acid generators, alone or combined with a thermal radical catalyst such as an azonitrile compound.

In the case of a thermally catalyzed radical polymerization of the (meth)acrylate monomers, the radical polymerization and the Claisen Rearrangement may be conducted in a single step. However, for most applications, it is contemplated that the radical polymerization will be conducted at a temperature lower than the rearrangement temperature, typically from about ambient to about 100° C.

Other conventional additives for adhesive, sealant or coating formulations may be added. Use of such additives will depend on the specific application for which the formulation is intended. Exemplary of such additives are thickeners, pigments, dyes, reinforcing and non-reinforcing fillers, viscosity modifiers, adhesion promoters or preventatives, odor masks, fragrances, tackifying agents, and the like.

The radically polymerized polymers of the inventive mono(meth)acrylic monomers of formulae I and/or II, above, generally a have very low degree of crosslinking and remain soluble in the monomer. Thus such polymers may be used as thickeners for curable monomer formulations. The monomers of such formulations may be monomers having both (meth)acrylic and allylic phenyl ether functionality or any other (meth)acrylic monomers in which the polymer is soluble.

The invention may be further illustrated by the following non-limiting examples.

EXAMPLE 1 Synthesis and polymerization of 4-allyloxybenzyl methacrylate (ABMA)

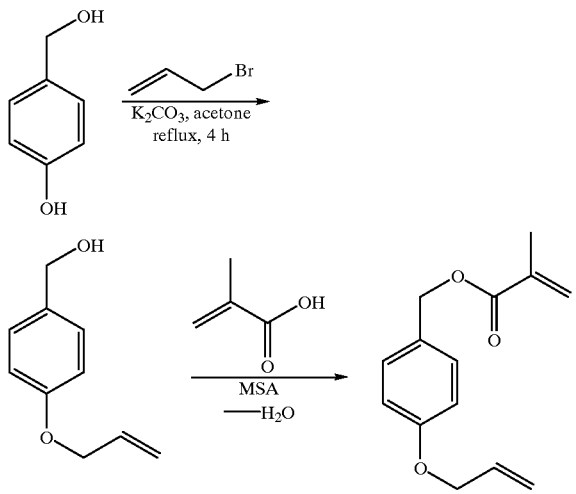

4-Allyloxybenzyl methacrylate was prepared in high yield by direct esterification of 4-allyloxybenzyl alcohol with methacrylic acid. The intermediate 4-allyloxybenzyl alcohol was prepared by alkylation of 4-hydroxybenzyl alcohol with allyl bromide. The details of these reactions were as follows:

Acetone (650 ml) and 4-hydroxybenzyl alcohol(99.0 g; 0.81 moles) were added to a 2 liter reactor fitted with a mechanical stirrer, reflux condenser, thermocouple probe and pressure-compensating addition funnel. The mixture was stirred and when the alcohol was dissolved, anhydrous potassium carbonate (111.2 g; 0.81 moles) was added in small portions to form a dispersion in the solution. Allyl bromide (97.6 g; 0.81 moles) (freshly purified by passing through a column of neutral alumina) was added slowly over one hour and the mixture heated under reflux for 4 hours. The mixture was cooled and filtered. The solvent was removed from the filtrate by distillation under reduced pressure to give an orange colored oil (89.7 g). The oil was purified by vacuum fractionation to give 4-allyloxybenzyl alcohol (59.9 g; 45% yield; b.p. 120° C. at 0.3 torr). The structure of the product was confirmed by 1H NMR and IR spectroscopy and purity, determined by GC, was 98%.

To a 250 ml reaction flask fitted with a Dean-Stark water trap, condenser and magnetic stirrer was added toluene (100 ml), 4allyloxybenzyl alcohol (30.0 g; 0.18 moles), methacrylic acid (15.7 g; 0.18 moles), 4-methoxyphenol (0.6 g) and p-toluene sulfonic acid (0.23 g). The stirred solution was heated under reflux until all of the water was removed (2 hours). The solution was cooled and washed with an equal volume of sodium bicarbonate solution and then with sodium chloride solution. The organic layer was dried over magnesium sulfate and the solvent removed by distillation under reduced pressure to yield 4-allyloxybenzyl methacrylate (33.6 g; 81% yield) as an orange colored viscous liquid.

In order to evaluate the thermal resistance properties of the new material, dynamic TGA was performed on ABMA (A+B cure) and benzyl methacrylate (BMA) (A cure only). Both compositions were formulated with identical initiator systems and A-stage cured under identical UV conditions. Commercially available poly(methyl methacrylate) (PMMA) was also included for additional comparison. The TGA traces, heating rate =10° C./min.; $N_2$ purge, are shown in FIG. 1.

The onsets of thermal decomposition for the three polymer samples were as follows: ABMA=430° C.; BMA=337° C.; PMMA=285° C. These results clearly indicate the superior thermal properties of the new material compared to non-phenolic methacrylates.

EXAMPLE 2 Synthesis of 4-allyloxyphenethyl methacylate (AOPMA)

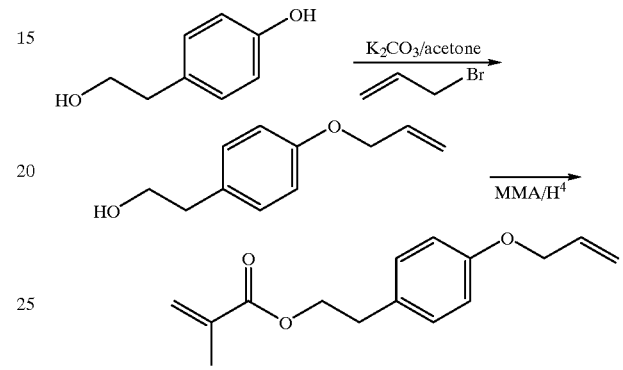

The two-step synthetic procedure of Example 1 was repeated starting with 2-(4-hydroxyphenyl)ethyl alcohol. In this case 1.2 equivalents of allyl bromide was employed in the alkylation step and the intermediate 4-allyloxyphenethyl alcohol was obtained in 77% yield following vacuum distillation (104–112° C. at 0.2 torr). Esterification of the alcohol with methacrylic acid afforded 4-allyloxyphenethyl methacrylate (AOPMA) in 88% yield.

EXAMPLE 3 Synthesis and Polymerization of 2-Allyloxybenzyl Methacrylate

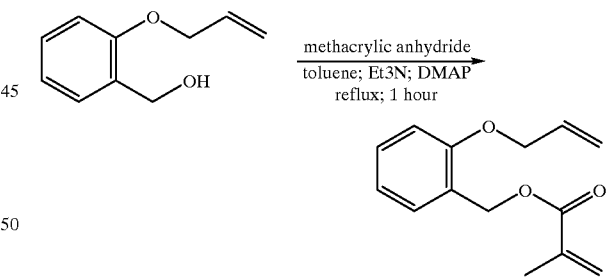

The ortho-substituted intermediate,2-allyloxybenzyl alcohol was prepared in 94% yield from 2-hydroxybenzyl alcohol and allyl bromide according to the procedure described in Example 2. The alcohol was esterified with methacrylic anhydride according to the following procedure:

To a 250 ml reaction flask fitted with a magnetic stirrer, thermocouple probe, addition funnel and reflux condenser was added 2-allyloxybenzyl alcohol (20.0 g; 0.12 moles), triethylamine (13.6 g; 0.13 moles), 4-dimethylaminopyridine (1.46 g; 0.012 moles), 2,6-di-tert-butyl-4-methylphenol (0.57 g; 2.6 m moles) and toluene (50 ml). The mixture was stirred to give a clear solution and methacrylic anhydride (22.0 g; 0.14 moles) was added dropwise over 15 minutes. The temperature increased from 24 to 51° C. and the solution turned light yellow in color during the addition. The solution was heated to reflux for 3.5 hours, cooled to ambient temperature and washed with 1M hydrochloric acid (30 mls) and then repeatedly with water (100 ml portions) until the water extracts indicated a neutral pH reaction. The resultant organic component was dried over magnesium sulfate, filtered and the solvent removed by evaporation under reduced pressure to yield 2-allyloxybenzyl methacrylate (22.7 g; 82% yield). The structure of the product was confirmed spectroscopically and GC analysis indicated a purity of 84%.

Figure 2:
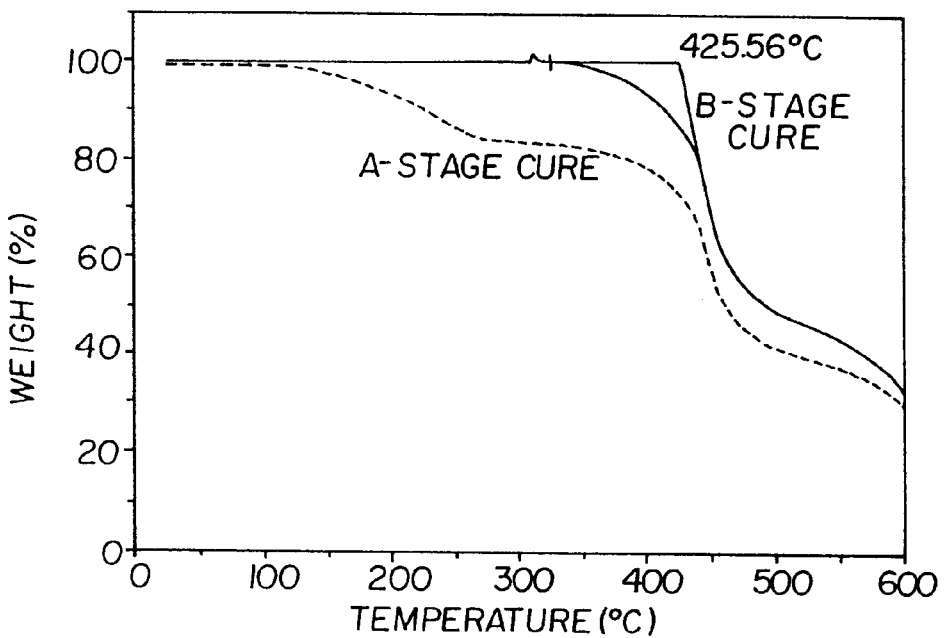
FIG. 2 is a TGA thermogram of an A-stage cured polymer of the invention and of the same polymer after B-stage curing, as described in Example 3.

A UV curable composition was prepared by dissolving 2% by weight each of free radical photoinitiator Darocure 1173) and cationic photocatalyst (Cyracure UVI-6974) in 2-allyloxybenzyl methacrylate. The composition was cured by UV exposure for several minutes (A-stage) followed by a post-cure by heating for 1 hour at 200° C. TGA was conducted on the A and B-staged material and the thermograms are shown in FIG. 2. The A-staged polymer shows an initial weight loss of about 15% between 150 and 200° C. Since this is greater than the expected loss from volatile initiator residues, it can be attributed to impurities in the monomer. After post-curing at 200° C. for 1 hour, the polymer shows no volatile emissions and the onset of decomposition occurs at the expected temperature of 425° C. IR analysis of the polymer during A and B stage curing confirms that the expected Claisen Rearrangement and formation of phenolic polymer occurs.

EXAMPLE 4 Synthesis of 2-(Allyloxyphenoxy) ethyl Methacrylate

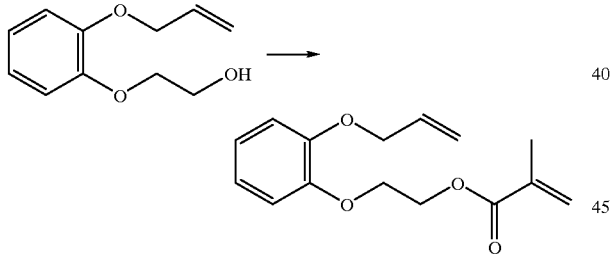

2-(Allyloxyphenoxy)ethyl methacrylate was prepared by esterification of 2-allyloxy-(2'-hydroxyethoxy)benzene with methacrylic anhydride by the procedure described in Example 3. The monomer was obtained in 91% yield and 91% purity (GC). The intermediate 2-allyloxy-(2'-hydroxyethoxy )benzene was synthesized in 98% yield by alkylation of 2-(2'-hydroxyethoxy)phenol with allyl bromide according to the procedure described in Example 2.

EXAMPLE 5 Synthesis of 4-Allyloxyphenethyl methacrylate (AOPMA)

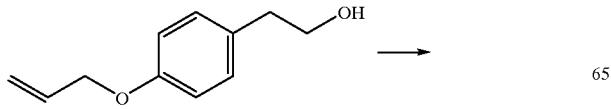

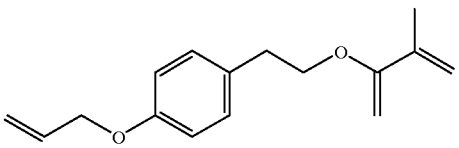

Allyloxyphenethyl methacrylate, 82% purity, was prepared in the manner of Example 3 from 2-(4-allyloxyphenyl) ethyl alcohol. The starting 2-(4-allyloxyphenyl)ethyl alcohol was prepared by alkylation of the corresponding phenolic alcohol with allyl bromide.

EXAMPLE 6 Synthesis of 4-Alyloxyphenyl Methacrylate

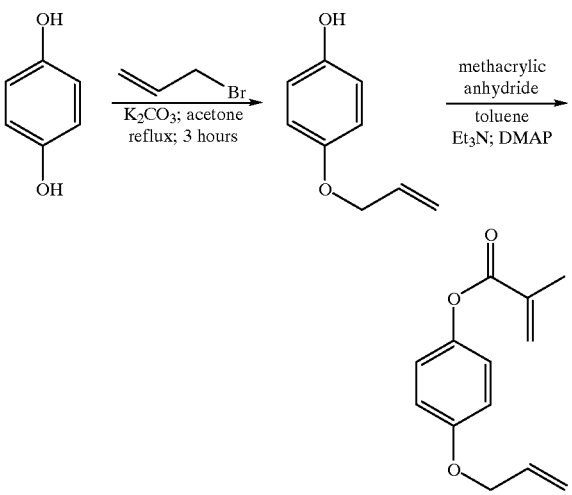

4-Allyloxyphenyl Methacrylate was synthesized as follows:

To a 1 liter reactor fitted with a mechanical stirrer, thermocouple probe, reflux condenser and addition funnel was added 1,4-hydroquinone (55.0 g, 0.50 moles) and acetone (400 ml). The mixture was stirred and anhydrous potassium carbonate (41.4 g; 0.30 moles) was added in small portions to form a dispersion in the acetone solution. The addition of the carbonate was accompanied by the formation of an orange color. Allyl bromide (63.53 g; 0.53 moles) (freshly purified by passing through a column of neutral alumina) was added slowly over one hour and the mixture heated under reflux for 7 hours. The mixture was cooled and filtered and the filtrate concentrated by distillation under reduced pressure until a solid material precipitated from solution. Toluene (250 ml) was added and the mixture filtered. The solvents were removed by distillation under reduced pressure and the residue distilled under vacuum to give a low melting solid. GC analysis showed this to be a 3:2 blend of 4-allyloxyphenol and 1,4-diallyloxybenzene (33.6 g). The blend was dissolved in toluene (90 ml) and extracted with cold dilute sodium hydroxide solution (3×75 ml; 0.2M). The caustic extracts were combined, neutralized with dilute hydrochloric acid (to pH=7) and extracted with toluene (4×100 ml). The combined toluene extracts were dried over magnesium sulfate and the solvent removed by distillation under reduced pressure to give crude 4-allyloxyphenol (15.7 g; 42% yield) as a brown colored solid (m.p. 34–37° C.). The crude material was distilled under vacuum to give 95% pure 4-allyloxyphenol (12.0 g; 32% yield). The structure of the product was confirmed by proton and infrared spectral analysis.

Methacrylic anhydride (6.92 g; 0.045 moles) was added dropwise to a chilled solution of purified 4-allyloxyphenol (7.0 g; 0.047 moles), triethylamine (3.55 g; 0.035 moles), 4-dimethylaminopyridine (0.43 g; 0.004 moles), 2-6-di-tert-butyl-4-methylphenol (0.018 g; 0.08 m moles) and toluene (20 ml) in a stirred 100 ml reaction flask fitted with a reflux condenser, magnetic stirrer and thermocouple probe. During the addition the reaction temperature increased to 37° C. The mixture was heated at 110° C. for 1.5 hour, cooled and washed sequentially with equal volumes of saturated sodium bicarbonate, dilute hydrochloric acid and water. The solution was dried over magnesium sulfate and the solvent removed under reduced pressure to yield 4-allyloxyphenyl methacrylate (8.3 g; 90% yield) as a clear yellow liquid. The structure of the monomer was confirmed by proton and infrared spectral analysis and GC analysis indicated a purity of 90%.

ANAEROBIC ADHESIVE FORMULATIONS

EXAMPLE 7

The monomer, 4-allyloxyphenethyl methacrylate (AOPMA) was prepared by direct esterification of 4-allyloxyphenethyl alcohol with methacrylic acid as previously described. Model anaerobic compositions were prepared from AOPMA and polyethylene glycol dimethacrylate (PEGMA) with an anaerobic cure system comprised of cumene hydroperoxide (1.5%), saccharin (1%) and dimethyl-p-toluidine (1%). Blends of these compositions were prepared to give adhesives with varying concentrations of AOPMA (25, 50, and 75%). Stabilizers were not employed in these initial formulations. However, the compositions all remained liquid over a period of several days and were found to fixture steel nuts and bolts after several hours at room temperature.

Figure 3:
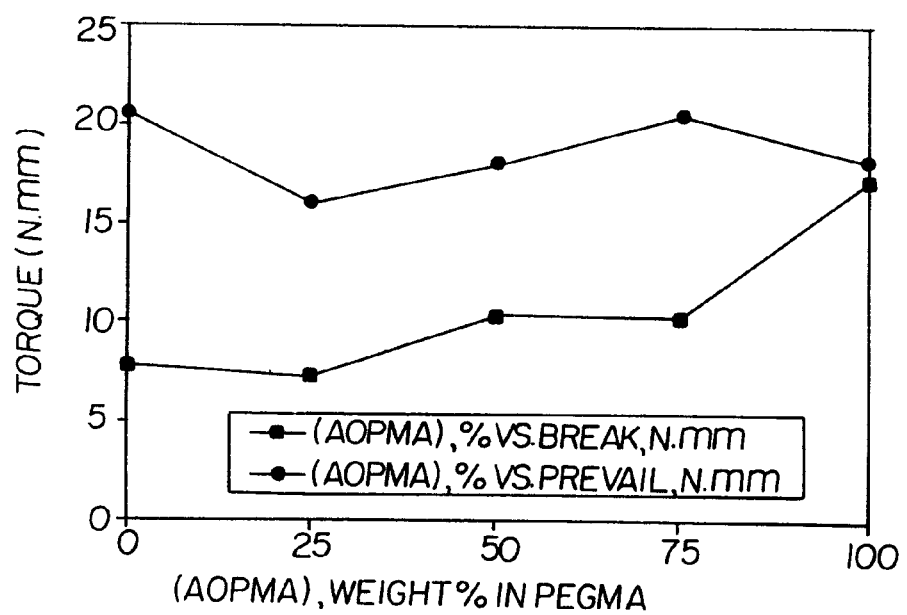
FIGS. 3–5 are graphs depicting break and prevail torque test results on cured adhesive formulations, as a function of composition, as reported in Examples 7–9.

Torque tests were performed to determine the effect of increasing concentrations of AOPMA on threadlocking strength and to compare performance with the common anaerobic monomer PEGMA. Degreased steel nut and bolt specimens (⅜×16) were assembled and tested according to ASTM D-5649 (Torque Strength of Adhesives Used on Threaded Fasteners). The assembled specimens were allowed to stand at 22° C. for 24 hours and the break and prevailing torque values were determined using a calibrated automated torque analyzer. The values recorded are the average measurements of 5 specimens. The results are shown in FIG. 3.

The break torque values were found to increase with increasing concentration of monofunctional AOPMA. This result is surprising, since it had been expected that the torque strength would decrease with increasing amounts of monofunctional monomer. The prevailing torques were found to remain essentially constant. These data show that AOPMA may be polymerized on steel threaded parts by an anaerobic cure system to modify existing anaerobic compositions without adversely affecting the cure chemistry.

EXAMPLE 8

Figure 4:
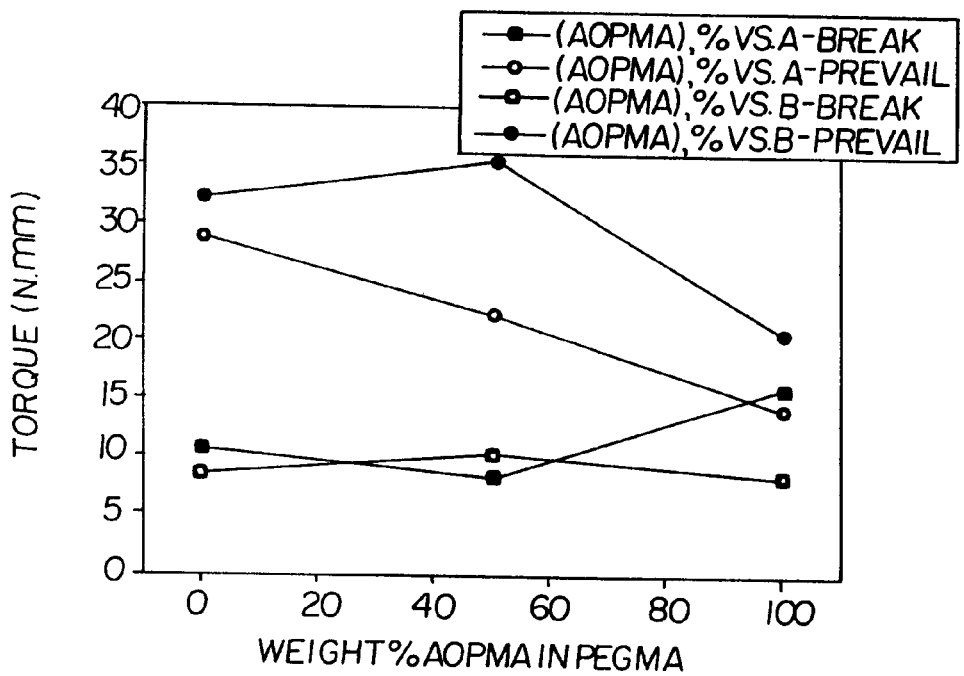

Anaerobic adhesive formulations were next prepared by adding, in addition to the anaerobic cure system components described above, 0.05% of 1,4-naphthoquinone to enhance the storage stability of the compositions. The monomers examined were PEGMA, a 1:1 blend of PEGMA and AOPMA and AOPMA alone. Torque tests were carried out following 20 hours RT cure (A-stage) and after additional heating at 200° C. for 3 hours (B-stage). The results, presented in FIG. 4, show the torque values as a function of AOPMA concentration. Break torque strengths for A-stage and B-stage cures are the same for PEGMA and the 1:1 blend. The corresponding value for AOPMA is significantly higher for the A-staged product, although the increased strength is lost during the B-stage curing. The prevailing strength following A-stage cure decreases uniformly with increasing concentration of AOPMA. IR analysis of A-stage cured AOPMA indicates consumption of methacrylate group with little or no loss of the allyloxy function.

On heating to 200° C. for 3 hours (B-stage cure), the prevailing strength of PEGMA remains essentially constant, whereas that of the 1:1 blend is enhanced compared to PEGMA or the A-stage blend. The prevailing torque of AOPMA product is also enhanced relative to the corresponding A-stage material, but is lower than that of PEGMA or the blend. This result suggests that optimal performance may be obtained with an anaerobic composition containing a blend of PEGMA and AOPMA. The IR spectrum of the B-stage product shows a strong absorption band at 3500 $cm^{-1}$, indicating the formation of phenolic material via Claisen Rearrangement. The improved performance of the B-stage AOPMA products is attributed to the phenol formation. In addition, the IR spectrum shows that the allyl group (1647 $cm^{-1}$) has been partially consumed during the B-stage process. The result suggests that an acid catalyst system may not be necessary to drive the B-stage chemistry.

EXAMPLE 9

Figure 5:
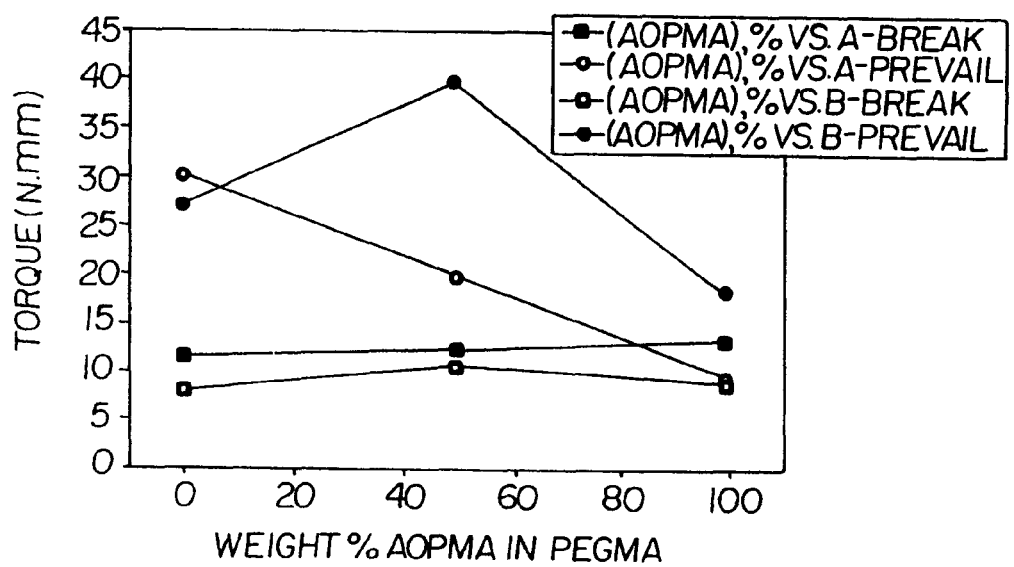

Similar experiments were carried out on anaerobic compositions containing a latent acid catalyst system in addition to the anaerobic cure system and stabilizers. The catalyst system was 0.5% AIBN and 1 % phenyl iodonium $SbF_6$, UV 9310. Cure conditions were A-stage cure =20 hr at 22° C.; B-stage cure =3 hr at 200° C. Torque strength results of this experiment are shown in FIG. 5.

The break torque values remain essentially constant during the two curing stages and independent of the adhesive composition. The prevailing torque for the A-stage material was found to decrease with increasing levels of AOPMA, as was observed for the equivalent composition without acid catalyst (see FIG. 4). The B-stage values for AOPMA and the 1:1 blend AOPMA/PEGMA are enhanced compared to the corresponding A-stage values. The composition containing the blend of monomers was found to have improved strength compared to PEGMA. IR analysis confirmed the expected chemical changes associated with the different cure stages.

These results confirm that active anaerobic compositions with comparative or even improved strength compared to PEGMA can be prepared from AOPMA or AOPMA/PEGMA blends. The monomer can be expected to enhance break torque values at all concentrations and prevailing torques at concentrations up to 50% loading after a B-stage cure cycle. The data also indicates that iodonium salts may be used as latent acid catalysts in compositions containing a conventional anaerobic cure system.

EXAMPLE 10

Heat-aging tests were completed on anaerobic adhesive compositions prepared with 4-allyloxyphenethyl methacrylate (AOPMA) and blends of AOPMA with PEGMA (compositions A and B). Details of the formulations are listed in Table 1. In addition to the conventional anaerobic curing agents, CHP, BS and DMPT small amount of AIBN (azobisisobutyronitrile) and UV9310 (phenyl iodonium hexafluoroantimonate salt) were also added to ensure the formation of acid catalyst during the heat curing cycle. Torque strength retention tests were performed on nut and bolt assemblies after 24 hours RT curing and weekly after heat aging at 200° C. for up to 6 weeks. Measurements were also made after 5 days at 250° C. The values obtained were compared to a control formulation prepared from PEGMA and cured under identical conditions (composition C). The tests were carried out using a calibrated automated torque analyzer according to ASTM D-5649 as already outlined.

TABLE 1

Formulation Details of Experimental Anaerobic Adhesive Products
(All concentrations are parts by weight)

| Formulation | A | B | C |
|---|---|---|---|
| AOPMA | 100 | 50 | 0 |
| PEGMA | 0 | 50 | 100 |
| CHP | 1.5 | 1.5 | 1.5 |
| BS | 1.0 | 1.0 | 1.0 |
| DMPT | 1.0 | 1.0 | 1.0 |
| AIBN | 0.5 | 0.5 | 0.5 |
| UV9310 | 1.0 | 1.0 | 1.0 |
| 1,4-Naphthaquinone | 0.05 | 0.05 | 0.05 |

Figure 6:
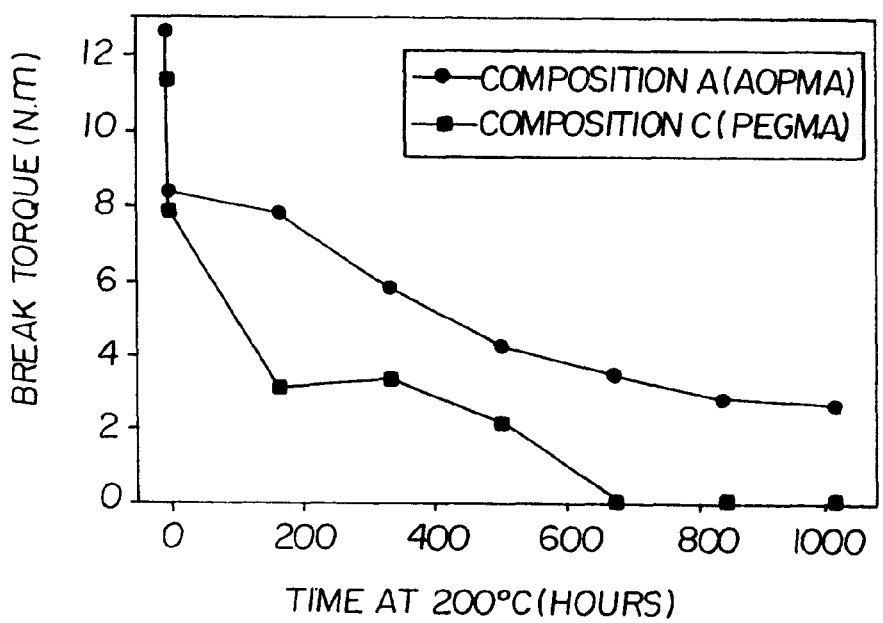
FIGS. 6–9 are graphs depicting break or prevail torque test results as a function of heat aging time at 200° C. for various compositions, as reported in Example 10.
Figure 7:
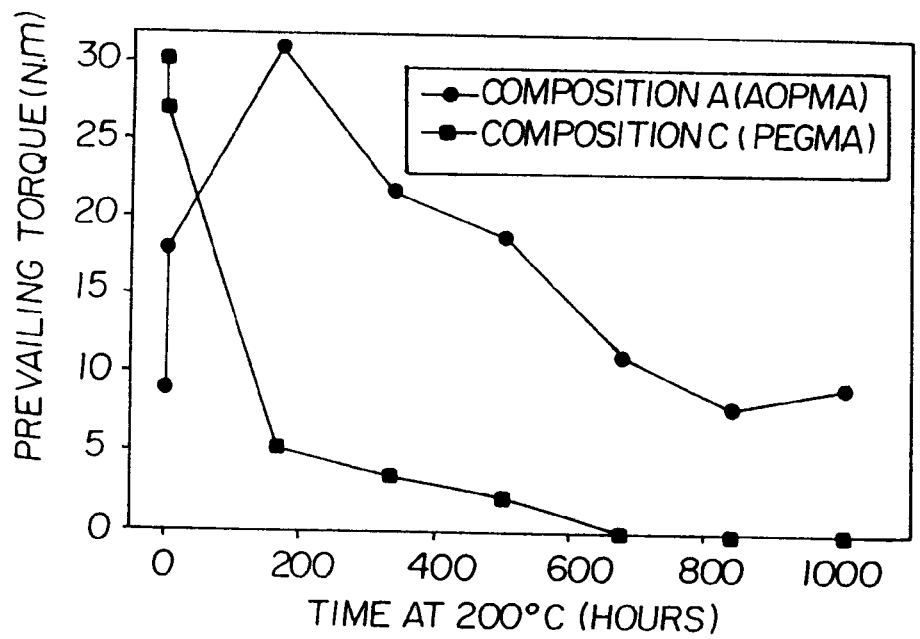

The results are shown in FIGS. 6–9. FIGS. 6 and 7 compare the performance of AOPMA (composition A) with the PEGMA control (composition C). After curing for 24 hours at RT, the break torque strength of AOPMA was found to be slightly higher than that of PEGMA (FIG. 6,). This result is surprising since AOPMA is mono-functional in methacrylate groups and is only lightly crosslinked following RT cure (IR analysis). In contrast, the di-functional PEGMA is more highly crosslinked after RT curing.

After heating at 200° C. for 3 hours, the break torque strengths of both products decrease significantly (FIG. 6). However, on continued heating, the break torque strength of the AOPMA composition decreases more slowly than the PEGMA control. After 1 week AOPMA retains about 66% of the original strength whereas PEGMA has about 25%. After 4 weeks at 200° C., the PEGMA composition has failed, whereas the AOPMA retains about 33% of its original value. After 6 weeks AOPMA still retains more than 20% of the original strength, thus indicating a superior performance compared to the control sample.

The prevailing torque value of AOPMA after RT cure is significantly lower than that of PEGMA following RT curing (FIG. 7). This is not surprising in view of the different crosslinked densities of the two products. However, on heating at 200° C., the two products behave in an entirely different manner. The prevailing torque strength of AOPMA rapidly increases, whereas that of PEGMA rapidly decreases. I R analysis confirms that AOPMA undergoes a post-curing reaction at these temperatures to form a highly crosslinked phenolic polymer. Thermal analysis of the phenolic material shows that it is particularly resistant to thermal degradation and the initial increase in prevailing torque and the relatively high retention of strength may be attributed to the formation of the phenolic material.

Figure 8:
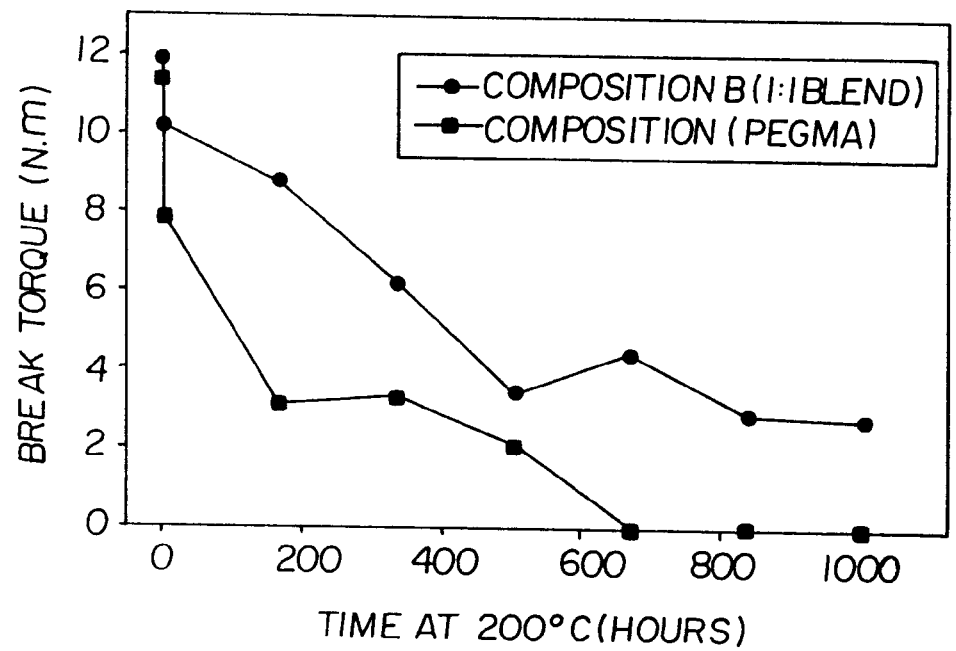
Figure 9:
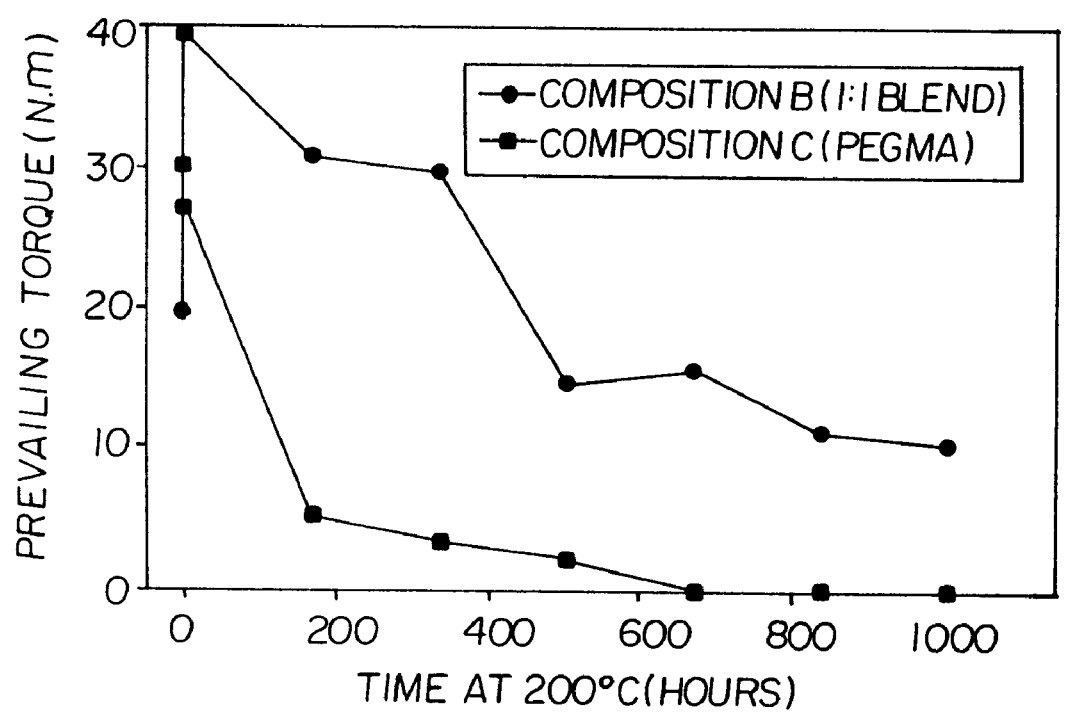

Similar results were obtained for the 1:1 blend of AOPMA and PEGMA (see FIGS. 8–9). In this case, the initial prevailing strength of the blend is significantly higher than that of the "pure" AOPMA. After 6 weeks at 200° C., the break-torque strength of the blend is 30% of its original RT cure value and the prevailing strength is 50% of its original value, whereas PEGMA fails after 4 weeks. These results demonstrate that AOPMA may be used as an additive in existing anaerobic adhesive formulations to enhance the thermal resistance properties of those materials.

What is claimed is:

1. A curable composition comprising:
   a) a monomer component comprising at least one compound selected from the group consisting of compounds of formulas I and II:

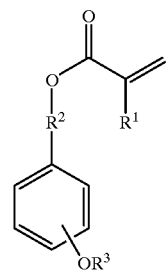

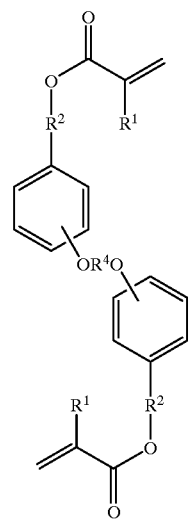

where $R^1$ is H or methyl; $R^2$ is a direct bond, a group of the formula —$C_nH_{2n}$—, or a group of the structure —$(OC_nH_{2n}$—$)_m$— which when taken with the phenyl group to which it is attached forms a phenyl ether; n is 1–4 and m is 1–10; $R^3$ is —$CH_2CH$=$CH_2$, —$CH_2C$ ($CH_3$)=$CH_2$, —$CH_2CH$=$CH(CH_3)$, —$CH_2C(CH_3)$=$CH(CH_3)$, —$CH_2CH$=$C(CH_3)_2$ or —$CH_2$ $CH$=$CH$ ($C_6H_5$); and $R^4$ is a divalent allylic group, and wherein the compound is optionally substituted on a phenyl group thereof by an alkyl, alkoxy or halo group, provided that relative to the respective —$OR^3$ or —$OR^4O$— groups, at least one unsubstituted ortho or para position remains on an adjacent phenyl ring; and
   b) a free radical catalyst system.

2. A composition as in claim 1 further comprising a latent acid catalyst.

3. A composition as in claim 2 wherein the latent acid catalyst is thermally activatable to produce said acid.

4. A method of curing a composition as in claim 1 comprising activating the free radical catalyst to induce polymerization of the monomer component at a temperature of less than 100° C., and subsequently heating the polymerized composition to a temperature of at least 100° C.

5. A method as in claim 4 wherein said subsequent heating temperature is at least 150° C.

6. A curable composition comprising:
a) at least one monomer compound having both (meth) acrylic ester functionality and an allylic phenyl ether functional group on the same molecule, the allylic phenyl ether functional group having at least one unsubstituted position on the phenyl ring which is ortho or para to the allylic ether group, and
b) a free radical catalyst system selected from the group consisting of anaerobic curing catalyst systems and free radical photoinitiator systems.

7. A curable composition as in claim 6 wherein said monomer compound a) is selected from the group consisting of
i) compounds represented by formulas I and II:

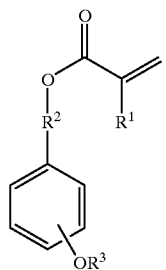

I

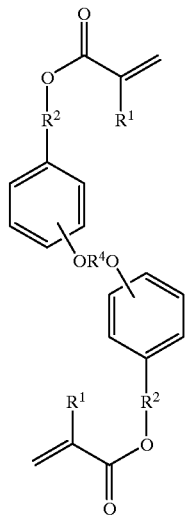

II where $R^1$ is H or methyl; $R^2$ is a direct bond, a group of the formula —$C_nH_{2n}$—, or a group of the formula —$(OC_nH_{2n})_m$— which when taken with the phenyl group to which it is attached forms a phenyl ether; n is 1–4 and m is 1–10; $R^3$ is —$CH_2CH=CH_2$, —$CH_2C(CH_3)=CH_2$, —$CH_2CH=CH(CH_3)$, —$CH_2C(CH_3)=CH(CH_3)$, —$CH_2CH=C(CH_3)_2$ or —$CH_2CH=CH(C_6H_5)$; and $R^4$ is a divalent allylic group, and wherein the compound is optionally substituted on a phenyl group thereof by an alkyl, alkoxy or halo group, provided that relative to the respective —$OR^3$ or —$OR^4O$— groups, at least one unsubstituted ortho or para position remains on an adjacent phenyl ring;

ii) the compounds:

4-(Prop-2-en-1-oxy)benzoic acid 4-methacryloxyphenyl ester

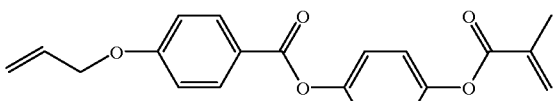

4-(Prop-2-en-1-oxy)benzoic acid 4-(4-methacryloxybiphenyl)ester

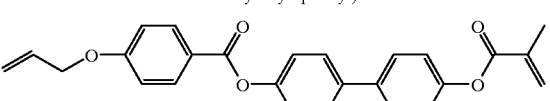

and
iii) mixtures of two or more of i) and ii).

8. A curable composition as in claim 6 wherein the free radical catalyst system is a free radical photoinitiator system.

9. A curable composition as in claim 6 wherein the free radical catalyst system is an anaerobic curing catalyst system.

10. A curable composition as in claim 6 further comprising a co-monomer which does not have allylic phenyl ether functionality and is co-curable with said monomer component a).

11. A composition as in claim 6 further comprising a latent acid catalyst.

12. A composition as in claim 11 wherein the latent acid catalyst is thermally activatable to produce said acid.

13. A method for bonding a pair of substrates comprising
i) applying a composition to a first of said substrates, the composition comprising
a) at least one monomer compound having both (meth) acrylic ester functionality and an allylic phenyl ether functional group on the same molecule, the allylic phenyl ether functional group having at least one unsubstituted position on the phenyl ring which is ortho or para to the allylic ether group, and
b) an anaerobic catalyst system or a free radical photoinitiator system;
ii) joining a second of said substrates to the first substrate with the applied composition therebetween and inducing curing of the applied composition to form a bonded assembly; and subsequently
iii) subjecting the bonded assembly to an elevated temperature of at least 100° C.

14. A method as in claim 13 wherein the composition further comprises a latent thermally activated acid generator.

15. A method as in claim 13 wherein said elevated temperature is at least 150° C.

16. A method as in claim 13 wherein component b) of said composition is an anaerobic catalyst system.

17. A method as in claim 13 wherein component b) of said composition is a free radical photoinitiator system and wherein curing of the applied composition is induced by exposure thereof to light in the UV-visible wavelength range.

18. A method of preparing a curable monomer comprising:
i) etherifying a phenolic hydroxyl group of a dihydroxybenzene or phenol alcohol with an allylic etherifying agent, to give a hydroxy-substituted allylic phenyl ether compound; and then
ii) esterifying said hydroxy-substituted allylic phenyl ether compound with an acrylic or methacrylic acylating agent.

19. A (meth)acrylic ester - allylic phenyl ether monomer of formulas I or II:

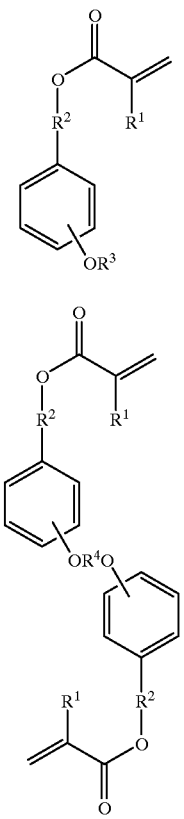

where $R^1$ is H or methyl; $R^2$ is a direct bond, a group of the formula $-C_nH_{2n}-$, or a group of the formula $-(OC_nH_{2n}-)_m-$ which when taken with the phenyl group to which it is attached forms a phenyl ether; n is 1–4 and m is 1–10; $R^3$ is $-CH_2CH=CH_2$, $-CH_2C(CH_3)=CH_2$, $-CH_2CH=CH(CH_3)$, $-CH_2C(CH_3)=CH(CH_3)$, $-CH_2CH=C(CH_3)_2$ or $-CH_2CH=CH(C_6H_5)$; and $R^4$ is a divalent allylic group, and wherein the compound is optionally substituted on a phenyl group thereof by an alky, alkoxy or halo group, provided that relative to the respective $-OR^3$ or $-OR^4O-$ groups, at least one unsubstituted ortho or para position remains on an adjacent phenyl ring.

20. A monomer as in claim 19 selected from the group consisting of 4-allyloxyphenethyl methacrylate, 3-allyloxyphenethyl methacrylate, 2-allyloxyphenethyl methacrylate, 4-allyloxyphenyl methacrylate, 3-allyloxyphenyl methacrylate, 2-allyloxyphenyl methacrylate, 2-(allyloxyphenoxy)ethyl methacrylate, 3-(allyloxyphenoxy)ethyl methacrylate, 4-(allyloxyphenoxy)ethyl methacrylate, 2-allyloxybenzyl methacrylate, 3-allyloxybenzyl methacrylate, and 4-allyloxybenzyl methacrylate.

21. A polymer produced by free-radical polymerization of a monomer composition comprising a (meth)acrylic ester - allylic phenyl ether monomer as in claim 19.

22. A polymer as in claim 21 wherein said (meth)acrylic ester - allylic phenyl ether monomer from which said polymer was produced is a monomer of formula I.

23. A polymer as in claim 22 wherein said (meth)acrylic ester - allylic phenyl ether monomer is selected from the group consisting of 4-allyloxyphenethyl methacrylate, 3-allyloxyphenethyl methacrylate, 2-allyloxyphenethyl methacrylate, 3-allyloxyphenyl methacrylate, 3-allyloxyphenyl methacrylate, 2-allyloxyphenyl methacrylate, 2-(allyloxyphenoxy)ethyl methacrylate, 3-(allyloxyphenoxy)ethyl methacrylate, 4-(allyloxyphenoxy)ethyl methacrylate, 2-allyloxybenzyl methacrylate, 3-allyloxybenzyl methacrylate, and 4-allyloxybenzyl methacrylate.

24. A curable composition comprising a polymer as in claim 21 dissolved in at least one (meth)acrylate monomer.

25. A curable composition as in claim 24 wherein the at least one (meth)acrylic monomer in which said polymer is dissolved comprises a monomer compound having both (meth)acrylic ester functionality and an allylic phenyl ether functional group on the same molecule, the allylic phenyl ether functional group having at least one unsubstituted position on the phenyl ring which is ortho or para to the allylic ether group.

26. A method of producing a polymer comprising free-radically A-stage curing a (meth)acylic ester - allylic phenyl ether monomer as in claim 19.

27. A method as in claim 26 wherein the polymer so produced is subsequently subjected to an elevated temperature of at least 100° C. to effect a B-stage curing of the polymer.

28. A method as in claim 27 wherein the polymer so produced is a component of a composition which further comprises a latent thermally activated acid generator.

29. A method as in claim 27 wherein said elevated temperature is at least 150° C.

* * * * *

UNITED STATES PATENT AND TRADEMARK OFFICE
CERTIFICATE OF CORRECTION

PATENT NO. : 6,231,714 B1
DATED : May 15, 2001
INVENTOR(S) : John G. Woods, Susanne Morrill, and Ciaran B. McArdle It is certified that error appears in the above-identified patent and that said Letters Patent is hereby corrected as shown below:

Column 4,
Line 44, delete "etherizing," insert -- etherifying --
Line 48, delete "esterifing," insert -- esterifying --
Line 55, delete "etherizing," insert -- etherifying --
Line 55, delete "("
Line 58, delete ")"

Column 5,
Line 2, delete "$(CH_2=C(CH_2ClS)_2)$" insert -- $(CH_2=C(CH_2Cl)_2)$ --

Column 20,
Line 19, delete "3," insert -- 4 --

Signed and Sealed this

Eleventh Day of December, 2001

Attest:

NICHOLAS P. GODICI
Attesting Officer     Acting Director of the United States Patent and Trademark Office